(12) United States Patent
Nowak

(10) Patent No.: US 12,329,944 B2
(45) Date of Patent: Jun. 17, 2025

(54) DRUG DELIVERY DEVICE HAVING PRESSURIZED VESSEL

(71) Applicant: AMGEN INC., Thousand Oaks, CA (US)

(72) Inventor: Gregory Thomas Nowak, Somerville, MA (US)

(73) Assignee: AMGEN INC., Thousand Oaks, CA (US)

( * ) Notice: Subject to any disclaimer, the term of this patent is extended or adjusted under 35 U.S.C. 154(b) by 525 days.

(21) Appl. No.: 17/626,966

(22) PCT Filed: Jul. 16, 2020

(86) PCT No.: PCT/US2020/042224
§ 371 (c)(1),
(2) Date: Jan. 13, 2022

(87) PCT Pub. No.: WO2021/011716
PCT Pub. Date: Jan. 21, 2021

(65) Prior Publication Data
US 2022/0362474 A1  Nov. 17, 2022

Related U.S. Application Data

(60) Provisional application No. 62/875,709, filed on Jul. 18, 2019.

(51) Int. Cl.
*A61M 5/31* (2006.01)
*A61M 5/142* (2006.01)
(Continued)

(52) U.S. Cl.
CPC .......... *A61M 5/31* (2013.01); *A61M 5/14244* (2013.01); *A61M 5/1452* (2013.01);
(Continued)

(58) Field of Classification Search
CPC .. A61M 5/31; A61M 5/14244; A61M 5/1452; A61M 5/145; A61M 5/2466;
(Continued)

(56) References Cited

U.S. PATENT DOCUMENTS

2008/0125727 A1  5/2008 Seibold et al.
2020/0164155 A1* 5/2020 Mojarrad ................ A61M 5/19

FOREIGN PATENT DOCUMENTS

WO  WO-2018164829 A1  9/2018
WO  WO-2019032482 A2 * 2/2019 ........ A61M 5/14244

OTHER PUBLICATIONS

International Search Report and Written Opinion for International Patent Application PCT/US2020/042224, dated Sep. 23, 2020.

* cited by examiner

*Primary Examiner* — Chelsea E Stinson
*Assistant Examiner* — Anh Bui
(74) *Attorney, Agent, or Firm* — MARSHALL, GERSTEIN & BORUN LLP

(57) ABSTRACT

A drive system for a drug delivery system includes a pressure chamber, a primary container, and a pressurized fluid. The pressure chamber has an outer surface and an inner surface that defines an interior volume. The primary container also has an outer surface and an inner surface that defines an interior volume to store a medicament to be administered to a user. The primary container is at least partially disposed within the interior volume of the pressure chamber. The pressurized fluid is disposed in the interior volume of the pressure chamber and is pressurized to exert a pressure on at least a portion of the outer surface of the primary container.

18 Claims, 2 Drawing Sheets

(51) Int. Cl.
  *A61M 5/145* (2006.01)
  *A61M 5/20* (2006.01)
(52) U.S. Cl.
  CPC ............... *A61M 2005/2086* (2013.01); *A61M 2005/3143* (2013.01); *A61M 2205/02* (2013.01); *A61M 2205/3331* (2013.01)
(58) Field of Classification Search
  CPC .......... A61M 5/288; A61M 2005/2086; A61M 2005/3143; A61M 2005/14252; A61M 2205/02; A61M 2205/3331
  See application file for complete search history.

DRUG DELIVERY DEVICE HAVING PRESSURIZED VESSEL

CROSS-REFERENCE TO RELATED APPLICATION

This is the United States national phase of International Patent Application No. PCT/US20/42224, filed on Jul. 16, 2020, which claims the priority benefit of U.S. Provisional Application No. 62/875,709, filed on Jul. 18, 2019, the entire contents of each of the foregoing being hereby incorporated by reference herein.

FIELD OF DISCLOSURE

The present disclosure generally relates to drug delivery devices and, more particularly, mechanisms and methods of delivery that reduce the risk of damage thereto.

BACKGROUND

Drug delivery devices, such as injectors, are used to deliver liquid drugs to a patient. Upon activation, drug delivery devices expel a drug stored within an internal reservoir known as a primary container through a needle, cannula, or other delivery member into the patient.

Some drug delivery devices, such as on-body injectors, may be temporarily attached to a patient to deliver a drug via an injection needle or some other means over an extended period of time. The drug delivery device may be adhesively attached to the tissue of the patient's abdomen, thigh, arm, or some other portion of the patient's body.

In some cases, the drug delivery device may be worn by the patient for several minutes or hours while the drug is administered to the patent. Viscous drugs, including some biologics, can require substantial forces to expel the drug from the drug delivery device, and thus may have longer injection times. As higher viscosity drugs are delivered via drug delivery devices, requisite driving forces needed to dispense the drug must also increase. These driving forces may place relatively large amounts of stress on the primary container, which may potentially cause damage to the container during drug delivery.

Other drug delivery devices, such as autoinjectors, may be used to deliver a drug into a patient over a relatively shorter period of time. However, autoinjectors may also require substantial forces to expel the drug from the drug delivery device and may also place relatively large amounts of stress on the primary container.

As described in more detail below, the present disclosure sets forth systems for delivery devices embodying advantageous alternatives to existing systems and methods, and that may address one or more of the challenges or needs mentioned herein, as well as provide other benefits and advantages.

SUMMARY

In accordance with a first aspect, a drive system for a drug delivery system includes a pressure chamber, a primary container, and a pressurized fluid. The pressure chamber has an outer surface and an inner surface that defines an interior volume. The primary container also has an outer surface and an inner surface that defines an interior volume to store a medicament to be administered to a user. The primary container is at least partially disposed within the interior volume of the pressure chamber. The pressurized fluid is disposed in the interior volume of the pressure chamber and is pressurized to exert a pressure on at least a portion of the outer surface of the primary container.

In some examples, the drive system further includes an insertion mechanism that is in fluid communication with the primary container. The insertion mechanism can include a needle or a cannula to be inserted into the user to deliver the medicament. Further, the drive system may further include an activation mechanism that is in fluid connection with the insertion mechanism and the primary container. The activation mechanism causes the insertion mechanism to insert the needle or cannula into the user and to cause the medicament to be dispensed.

In some forms, the drive system may additionally include a septum disposed at an end of the pressure chamber. Upon piercing the septum, a fluid flow path is formed from the interior volume of the primary container to the needle or the cannula.

In some examples, the drive system may include additional components such as a sealing member and/or a stopper member. The sealing member may be at least partially disposed within the interior volume of the pressure chamber to seal the interior volume of the pressure chamber from the interior volume of the primary container. The stopper member may be at least partially disposed within the interior volume of the pressure chamber to retain the pressurized fluid within the interior volume thereof.

In some approaches, the pressure chamber may be constructed from a transparent and/or a translucent material. The pressurized fluid may be water and/or a silicone gel, and may be pressurized to a pressure level that is a fraction of a failure point of the primary container.

In accordance with a second aspect, an approach for reducing damage to a primary container of a drug delivery device includes providing a pressure chamber having an outer surface and an inner surface defining an interior volume. A primary container is disposed in the interior volume of the pressure chamber. The primary container has an outer surface and an inner surface that defines an interior volume to store a medicament to be administered to a user. A fluid is pressurized to a desired fluid pressure value, and the fluid is then disposed in the pressure chamber such that the fluid at least partially surrounds at least a portion of the outer surface of the primary container.

In accordance with a third aspect, a drug delivery device includes a housing defining a shell and an inner volume, a pressure chamber at least partially disposed within the inner volume of the housing, a primary container, a pressurized fluid, an insertion mechanism, an activation mechanism, and a fluid flow connection. The pressure chamber includes an outer surface and an inner surface defining an interior volume. The primary container has an outer surface and an inner surface defining an interior volume to store a medicament to be administered to a user, and is at least partially disposed within the interior volume of the pressure chamber. The pressurized fluid is disposed in the interior volume of the pressure chamber and is pressurized to exert a pressure on at least a portion of the outer surface of the primary container. The insertion mechanism is in fluid communication with the primary container and includes a needle or a cannula to be inserted into the user to deliver the medicament. The activation mechanism is in fluid connection with the insertion mechanism and the primary container and is adapted to cause the insertion mechanism to insert the needle or cannula into the user and to cause the medicament to be dispensed. The fluid flow connection is coupled to the primary container and the needle or cannula and is adapted to allow the medicament to flow from the primary container to the needle or cannula.

BRIEF DESCRIPTION OF THE DRAWINGS

The above needs are at least partially met through provision of the drug delivery device having a pressurized vessel described in the following detailed description, particularly when studied in conjunction with the drawings, wherein.

The accompanying figures show embodiments according to the disclosure and are exemplary rather than limiting.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

The present disclosure generally relates to a drive system for a drug delivery device. In one embodiment, an on-body drug delivery device generally includes a housing defining a shell and an inner volume, a drive system, an insertion mechanism, an activation mechanism, and a fluid flow connection, each of which is at least partially disposed within the housing. The drive system includes a pressure vessel or chamber, a primary container to store the medicament to be administered to the user, and a pressurized fluid that at least partially surrounds the primary container within the pressure chamber. The pressure chamber, and the pressurized fluid contained therein, apply a compressive preloading force or pressure to the exterior of the primary container. This compressive preload results in an adjusted pressure differential between the inside and the outside of the primary container, and in turn allows for the exertion of larger internal forces (via the drive mechanism urging the medicament out of the primary container), thereby reducing a likelihood of damage to the primary container. In other embodiments, an autoinjector delivery device generally includes similar components as the previously-described on-body drug delivery device such as a housing, a drive system, insertion and activation mechanisms, and a fluid flow connection. The drive system in these embodiments also includes a pressure chamber having an inner volume to accommodate a primary container and a pressurized fluid that applies a compressive force to the exterior of the primary container.

Figure 1:
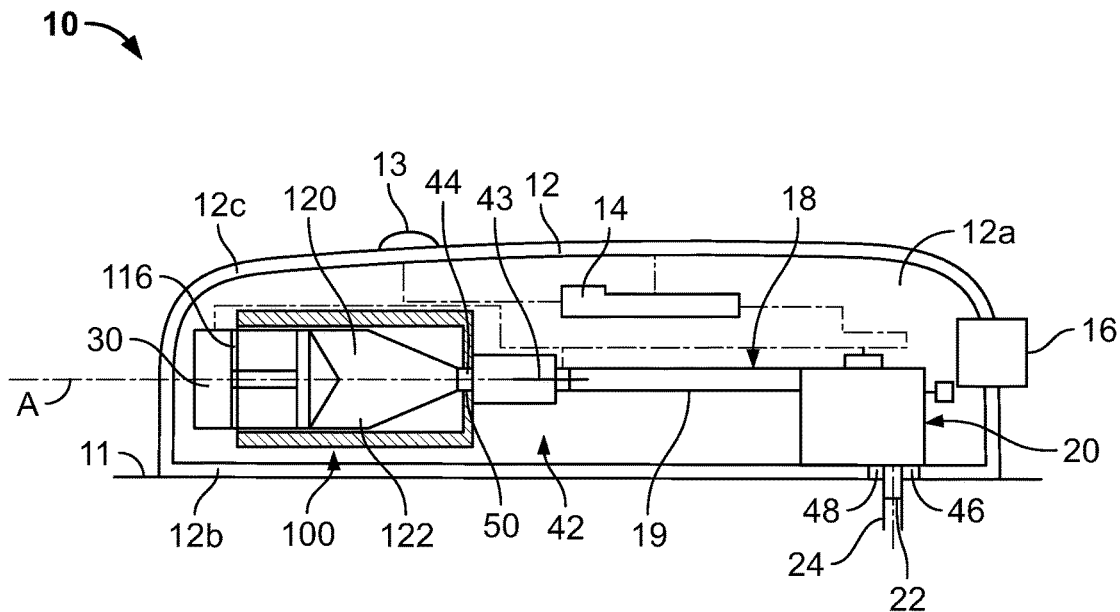
FIG. 1 illustrates a schematic representation of an example arrangement of a drug delivery device having a drive system including a pressurized chamber in accordance with various embodiments.
Figure 4:
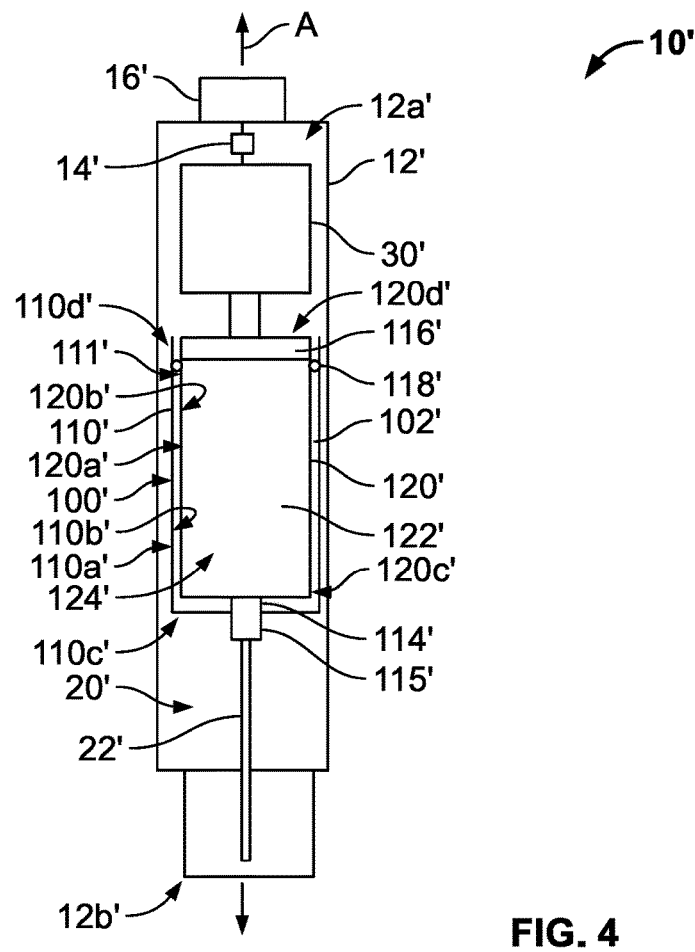
FIG. 4 illustrates a schematic representation of an alternative example arrangement of a drug delivery device having the example drive system depicted in FIGS. 2 and 3 in accordance with various embodiments.

Referring to FIG. 1, a general drug delivery device (e.g., a wearable drug delivery device 10) is provided that may include any number of aspects of the drive system herein described. In at least one example, the drug delivery device 10 may be configured as a wearable drug delivery device, such as an on-body injector, that may be attached to a patient's tissue 11 (e.g., the patient's skin) to administer delivery of a drug treatment. However, in other examples, the drug delivery device 10 may be in the form of an autoinjector or any other type of device (as illustrated in FIG. 4). The drug delivery device 10 may automatically deliver a subcutaneous injection of a fixed or a patient/operator-settable dose of a drug over a controlled or selected period of time. The drug delivery device 10 may be intended for self-administration by the patient, but may also be used by a caregiver or a formally trained healthcare provider to administer an injection.

The drug delivery device 10 has a housing 12 defining a shell and having an inner volume 12a, a needle insertion mechanism 20, an activation mechanism 30, and a drive system 100, each of which may be at least partially disposed within the housing 12. Further, the drug delivery device may include a controller 14 and an actuator 16 (e.g., a depressible button) that is arranged on an exterior of the housing 12.

Figure 2:
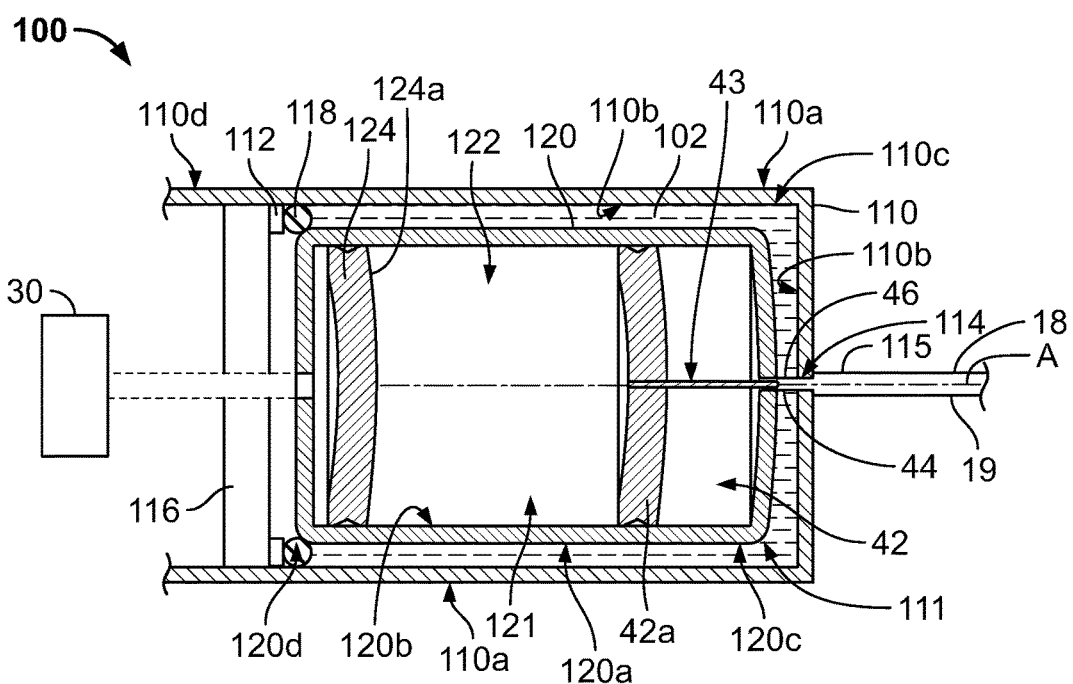
FIG. 2 illustrates an example drive system in a first, starting position in accordance with various embodiments.
Figure 3:
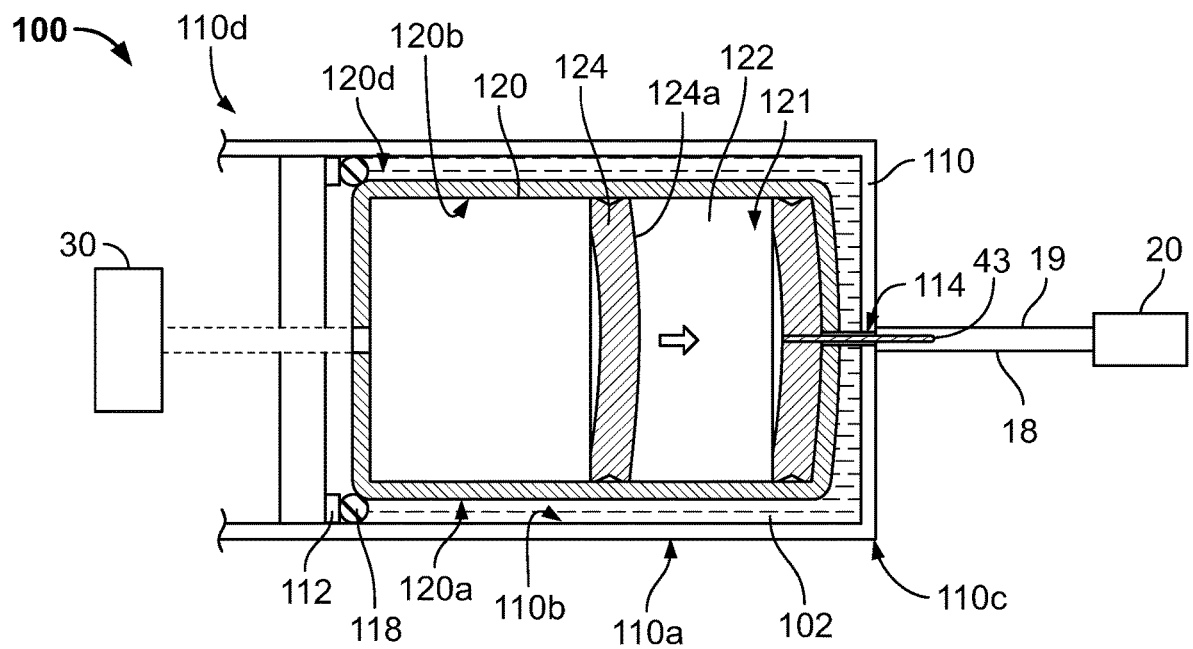
FIG. 3 illustrates the example drive system of FIG. 2 during drug administration in accordance with various embodiments.

With brief reference to FIGS. 2 and 3, the drive system 100 includes a pressure chamber 110, a primary container 120, and a pressurized fluid 102. The pressure chamber 110 has an outer surface 110a, an inner surface 110b that defines an interior volume 111, a first end 110c, and a second end 110d. The primary container 120 has an outer surface 120a, an inner surface 120b that defines an interior volume 121, a first end 120c, and a second end 120d. The pressure chamber 110 and the primary container 120 will be discussed in further detail below.

Returning again to FIG. 1, the housing 12 may include a bottom wall 12b to be releasably attached (e.g., adhered with an adhesive) to the patient's skin 11, and a top wall 12c including one or more visual feedback mechanisms 13 such as, for example a window, an opening, and/or an illumination system (not illustrated) for viewing the primary container 120 and the drug contained therein. The one or more visual feedback mechanisms 13 may be used to communicate information to the user about the operational state of the drug delivery device 10 and/or the condition of the medicament or drug. An opening 46 may be formed in the bottom wall 12b, and optionally a septum 48 may extend across the opening 46 to seal the interior of the housing 12 prior to use. In some embodiments, the pierceable sterile barrier 48 may be omitted, and instead a removable sealing member (not illustrated) may cover and seal closed the opening 46 prior to use. The exterior of the needle insertion mechanism 20 may be defined by an insertion/retraction mechanism housing that is separate from the housing 12.

A fluid pathway connector 18 connects the drive system 100, and more specifically the primary container 120, to the needle insertion mechanism 20. The actuator 16 is configured to initiate operation of the drug delivery device 10 by activating, via mechanical and/or electrical means (shown in dotted lines in FIG. 1), the activation mechanism 30, the needle insertion mechanism 20, the controller 14, and/or other mechanisms and/or electronics. In some examples, wireless communication may be employed to cause the device 10 to be activated. In embodiments where the actuator 16 is a button that is depressed or otherwise physically moved by a user or patient, the actuator 16 may be configured to exert a motive force needed to activate the needle insertion mechanism 20, the fluid pathway connector 18, the activation mechanism 30, the controller 14, and/or other mechanisms. In such embodiments, the actuator 16 may be physically connected to, either directly or indirectly via a mechanical linkage, the needle insertion mechanism 20, the activation mechanism 30, the fluid pathway connector 18, and/or other mechanisms such that manually depressing or otherwise interacting with the actuator 16 supplies the motive force necessary to activate the needle insertion mechanism 20, the activation mechanism 30, the fluid pathway connector 18, and/or other mechanisms.

The fluid pathway connector 18 defines a sterile fluid flow path 19 between the primary container 120 and the needle insertion mechanism 20. The fluid pathway connector 18 may include a container access mechanism 42 configured to insert a container needle 43 through a septum 44 associated with and/or covering the primary container 120 and/or the pressure chamber 110 to establish fluid communication between the primary container 120 and the sterile fluid flow path 19 in response to activation of the drug delivery device 10, for example, via the actuator 16. In the illustrated example of FIGS. 2 and 3, the primary container 120 includes a movable element 42a that is coupled to the container needle 43 which moves to pierce the septum 44. In some examples, the needle insertion mechanism 20 and the primary container 120 and/or other components of the drive system 100 may be integrated into a single unit, and thus the fluid pathway connector 18 may not be incorporated into the drug delivery device 10.

For example, in some embodiments, manually depressing the actuator 16 may cause the fluid pathway connector 18 to move towards the first end 120c of the primary container 120, or cause the primary container 120 to move towards the fluid pathway connector 18, and thereby cause the container needle 43 to penetrate through the seal member or septum 44 into the reservoir or interior volume 121 of the primary container 120. Additionally, or alternatively, the actuator 16 may operate as an input device that transmits an electrical and/or mechanical signal to the controller 14, which in turn may execute programmable instructions to control operation of the needle insertion mechanism 20, the activation mechanism 30, the fluid pathway connector 18, and/or other mechanisms. In such embodiments, the controller 14 may include a processor (e.g., a microprocessor) and a non-transitory memory for storing the programmable instructions to be executed by the processor. Furthermore, in such embodiments, the drug delivery device 10 may include an internal actuator (e.g., an electric motor, a pneumatic or hydraulic pump, and/or a source of pressurized gas or liquid) which is separate from the actuator 16 and which, in response to an electrical control signal received from the controller 14, exerts the motive force needed to activate the needle insertion mechanism 20, the activation mechanism 30, the fluid pathway connector 18, and/or other mechanisms.

The activation mechanism 30 may include any number of components and/or sub-components to drive, urge, and/or exert a force on the primary container 120 to cause a drug or medicament 122 stored therein to be dispensed therefrom. For example, the activation mechanism 30 may be in the form of a hydro-pneumatic actuation system whereby a hydraulic and/or pneumatic force is exerted on the primary container 120. In other examples, the activation mechanism 30 may include any number of resilient members (e.g., springs) that exert an urging force, directly and/or indirectly, onto the primary container 120. Examples of suitable activation mechanisms 30 are described in U.S. App. No. 62/543,058, filed on Aug. 9, 2017, the entire contents of which are incorporated by reference herein. Other examples of suitable activation mechanisms 30 are possible.

Upon activation of the drug delivery device 10, the drug delivery device 10 may enable, connect, or open necessary connections to establish fluid communication between the primary container 120 and the fluid pathway connector 18. Simultaneously or subsequently, the needle insertion mechanism 20 may insert a needle 22 into the patient 11, which may be a rigid or a flexible needle 22. In examples using a flexible needle 22, the flexible needle 22 may be constructed from a super-elastic material such as nitinol, a polymer, or another material that allows the needle to follow a curved path without sustaining damage. Next, the activation mechanism 30 may force a drug or medicament 122 stored in the primary container 120 through the sterile fluid flow path 19 of the fluid pathway connector 18 and into the needle insertion mechanism 20 for subcutaneous delivery to the patient 11.

After the bottom wall 12b of the housing 12 is attached to the patient's skin 11, the needle insertion mechanism 20 may be activated to move a delivery member from a retracted position within the housing 12 to a deployed position extending outside of the housing 12. In the present embodiment, this may include the needle insertion mechanism inserting the needle or trocar 22 and/or a hollow cannula 24 through the septum 48 and into the patient's skin 11 and subcutaneous tissue 13, as illustrated in FIG. 1. Immediately or shortly thereafter, the needle insertion mechanism 20 may automatically retract the needle 22, leaving the distal open end of the cannula 24 inside the patient for subcutaneous delivery of the drug 122. The needle 22 may be solid and have a sharpened end for piercing the patient's skin 11. Furthermore, the needle 22 may be made of a material that is more rigid than the cannula 24. In some embodiments, the needle 22 may be made of metal, whereas the cannula 24 may be made of plastic or another polymer. The relative flexibility of the cannula 24 may allow it to be disposed subcutaneously within the patient's tissue 11 for a period of a time without causing pain or significant discomfort to the patient.

In some embodiments, the needle insertion mechanism 20 may include one or more springs (e.g., coil springs, torsion springs, etc.; not shown) initially retained in an energized state, and which are released upon depression of the actuator 16 in order to insert the needle 22 and cannula 24, or hollow needle, into the patient. Furthermore, retraction of the needle 22 may be achieved by the automatic release of another spring after the needle 22 and cannula 24 have been inserted into the patient. Other power sources for insertion and/or retraction are possible, including, for example, an electric motor, a hydraulic or pneumatic pump, or a canister that releases a pressurized gas or pressurized liquid to provide actuation energy.

As previously noted, the primary container 120 includes a wall having the outer surface 120a and the inner surface 120b defining an interior volume 121 that is filled with the drug 122. In some embodiments, the interior volume 121 may be pre-filled with the drug 122 by a drug manufacturer prior to installation of the primary container 120 in the drug delivery device 10. In some embodiments, the primary container 120 may be rigidly connected to the housing 12 such that the primary container 120 cannot move relative to the housing 12; whereas, in other embodiments, the primary container 120 may be slidably connected to the housing 12 such that the primary container 120 can move relative to the housing 12 during operation of the drug delivery device 10. The primary container 120 may have an elongate, barrel-like or cylindrical shape extending along a longitudinal axis A. In embodiments where the drug delivery device 10 is configured as an on-body injector, the longitudinal axis A of the primary container 120 may be perpendicular or substantially perpendicular, or otherwise non-parallel, to a direction in which the needle insertion mechanism 20 inserts a delivery member such as the cannula 24 into the patient 11. This configuration may allow the on-body injector to have a generally planar, low-profile shape that can be worn by the patient without impeding the patient's movement. Initially, a plunger 124 or other piston member may be positioned in the interior volume 121 at the second end 120*d* of the primary container 120. The plunger 124 may sealingly and slidably engage the inner surface 120*b* of the wall of the primary container 120, and may be movable relative to the wall. Put differently, the plunger 124 acts as a seal that restricts the drug 122 from exiting the second end 120*d* of the primary container 120.

The volume of the drug 122 contained in the interior volume 121 prior to delivery may be: any volume in a range between approximately (e.g., ±10%) 0.5-20 mL, or any volume in a range between approximately (e.g., ±10%) 0.5-10 mL, or any volume in a range between approximately (e.g., ±10%) 1-10 mL, or any volume in a range between approximately (e.g., ±10%) 1-8 mL, or any volume in a range between approximately (e.g., ±10%) 1-5 mL, or any volume in a range between approximately (e.g., ±10%) 1-3.5 mL, or any volume in a range between approximately (e.g., ±10%) 1-3 mL, or any volume in a range between approximately (e.g., ±10%) 1-2.5 mL, or any volume in a range between approximately (e.g., ±10%) 1-2 mL, or any volume equal to or less than approximately (e.g., ±10%) 4 mL, or any volume equal to or less than approximately (e.g., ±10%) 3.5 mL, or any volume equal to or less than approximately (e.g., ±10%) 3 mL, or any volume equal to or less than approximately (e.g., ±10%) 2.5 mL, or any volume equal to or less than approximately (e.g., ±10%) 2 mL, or any volume equal to or less than approximately (e.g., ±10%) 1.5 mL, or any volume equal to or less than approximately (e.g., ±10%) 1 mL, or any volume equal to or greater than approximately (e.g., ±10%) 2 mL, or any volume equal to or greater than approximately (e.g., ±10%) 2.5 mL, or any volume equal to or greater than approximately (e.g., ±10%) 3 mL. The interior volume 121 may be completely or partially filled with the drug 122. The drug 122 may be one or more of the drugs listed below under the heading "Drug Information", such as, for example, a granulocyte colony-stimulating factor (G-CSF), a PCSK9 (Proprotein Convertase Subtilisin/Kexin Type 9) specific antibody, a sclerostin antibody, or a calcitonin gene-related peptide (CGRP) antibody.

The pressure chamber 110 may be constructed from a generally transparent and/or translucent material such as a polymeric material that is capable of withstanding high pressures. By using a transparent and/or a translucent material, a user may be able to inspect the primary container 120 either directly or by looking through the visual feedback mechanism 13. The pressure chamber 110 includes a first end 110*c* and a generally-open second end 110*d*. As previously noted, the interior volume 111 of the pressure chamber 110 is dimensioned to accommodate at least a portion of the primary container 120 therein. In some examples, the pressure chamber 110 is configured to entirely encapsulate the primary container 120. The pressure chamber 110 further includes a ledge 112 and an opening 114 that is aligned with the container access mechanism 42 to allow the container needle 43 access to the drug 122. In some examples, the first end 110*c* of the pressure chamber 110 may also include a pierceable septum (not shown) that the container needle 43 pierces during activation.

The pressurized fluid 102 may be any type of generally incompressible or near-incompressible fluid such as water or silicone oil. In some embodiments, the pressurized fluid 102 is generally transparent or translucent to allow the user to inspect the primary container 120 either directly or by looking through the visual feedback mechanism 13. To properly pressurize the pressure chamber 110, the primary container 120 is inserted into the interior volume 111 of the pressure chamber 110 and is positioned such that the first end 120*c* of the primary container 120 is aligned with the first end 110*c* of the pressure chamber 110. A steady-flow mechanism (e.g., a nozzle or any other device) is used to insert the pressurized fluid 102 into the interior volume 111 of the pressure chamber 110 by setting a flow rate that corresponds to the desired pressure. The pressurized fluid 102 is urged through the interior volume 111 of the pressure chamber 110 (e.g., from the first end 110*c* to the second end 110*d* or vise-versa) until a desired flow rate is achieved, and subsequently, a stopper member 116 is positioned at the generally-open second end 110*d* of the pressure chamber 110 to seal and retain the pressurized fluid 102 therein. A septum 115 is then used the plug the opening 114 of the pressure chamber 110, and as such, the pressurized fluid 102 will remain in the interior volume 111 of the pressure chamber 110 while encapsulating and creating an urging force on the outer surface 120*a* of the primary container 120. A pressure gauge, a force transducer, and/or any other number of suitable components may be used to measure the flow rate of the pressurized fluid 102.

In some examples, a sealing member 118 such as an O-ring or other device may be positioned near the ledge 112 of the pressure chamber 110 or at any other location within the pressure chamber 110 to provide a seal that separates the interior volume 111 of the pressure chamber 110 from any region that the drug 122 may enter to reduce and/or eliminate potential contamination of the drug 122.

During operation of the drug delivery device 10, the activation mechanism 30 exerts a force on the second end 120*d* of primary container 120. For example, as illustrated in FIG. 3, the activation mechanism 30 may cause the plunger 124 to be urged along the longitudinal axis A from the second end 120*d* of the primary container 120 to the first end 120*c* of the primary container 120 in order to expel or urge the drug 122 from the primary container 120 (and towards the needle insertion mechanism 20). In some embodiments, the activation mechanism 30 may include one or more springs (e.g., coil springs, torsion springs, etc.) initially retained in an energized state, and which are released upon depression of the actuator 16. Following their release, the spring(s) may expand or contract to move the plunger 124 through the interior volume 121 along the longitudinal axis A. In other embodiments, the activation mechanism 30 may include an electric motor (not illustrated) which rotates a gear mechanism, including for example one or more sprocket gears, to cause axial motion of the stopper 124 through the interior volume 121. In still further embodiments, the activation mechanism 30 may include both an electric motor and spring(s), wherein the electric motor regulates expansion of the spring(s) via a tether or pulley system. In still further embodiments, the activation mechanism 30 may include a canister that releases a pressurized gas or pressurized liquid to provide actuation energy. Other examples are possible.

Nonetheless, in any of these embodiments, the stopper 124 exerts a force on the drug 122 that in turn exerts an outward force on the inner surface 110*b* of the primary container 120. As previously noted, the primary container 120 may only be capable of withstanding a limited pressure differential between the interior volume 121 and the exterior volume thereof before becoming susceptible to damage. As a non-limiting example, the primary container 120 may be capable of withstanding an outwardly-directed pressure of approximately 200 psi before incurring damage (e.g., failure, breaking, rupturing, etc.). However, by configuring the pressure chamber 110 to exert an inwardly-directed pressure onto the outer surface 120*a* of the primary container 120 an amount that is a fraction of this failure point (e.g., a fraction of approximately 5 psi), the pressure differential between the interior volume 121 of the primary container 120 and the volume external to the primary container 120 (i.e., the interior volume 111 of the pressure chamber 110). As a result, the primary container 120 may be capable of withstanding additional outwardly-directed pressures (e.g., up to approximately 15 psi) prior to incurring any damage.

As previously noted, the fluid pathway connector 18 is configured to establish fluid communication between the primary container 120 and the needle insertion mechanism 20 via a sterile fluid flow path 19 during operation of the drug delivery device 10. A first end 18*a* of the fluid pathway connector 18 may include the container needle 43 and an overmold member 50. In general, the overmold member 50 may serve as a mounting member or connection hub for the container needle 43 and provide a portion of the container needle 43 which does not access the interior volume 121 with an enlarged outer dimension, such as an enlarged outer diameter. The container needle 43 may have a sharpened end or point and a second end in fluid communication with the fluid flow connection.

The first end 18*a* of the fluid pathway connector 18 is connected to the first end 120*c* of the primary container 120 and a second end 18*b* is connected to a first end of the needle insertion mechanism 20. The fluid pathway connector 18 can incorporate any number of additional components such as, for example, a backflow prevention mechanism (not illustrated). The fluid flow path 19 may be sterilized, and may be partially or entirely made of a flexible tubing such as, for example, a polymer or other material. Initially, there may be slack in the flexible tubing to allow the fluid pathway connector 18 to move relative to the housing 12 and/or to allow components of the needle insertion mechanism 20, that the fluid pathway connector 18 is attached thereto, to move relative to the housing 12.

The drive system 100 may include any number of additional features to assist in proper operation. For example, the first end 110*c* of the pressure chamber 110 may be chamfered and/or dimensioned to closely match dimensions of the first end 120*c* of the primary container 120 to reduce and/or eliminate potential stress points. Stress concentration in the interior corners of the pressure chamber 110 may be reduced by placing a radius in the corners in contact with the pressurized fluid 102.

Turning to FIG. 4, an alternative example drug delivery device is provided that is in the form of an autoinjector drug delivery device 10' that includes similar features as the wearable drug delivery device 10 including the drive system 100. Accordingly, for the sake of brevity, more specific details of the components and operation of the autoinjector drug delivery device 10' will not be discussed in substantial detail. Like the wearable drug delivery device 10, the autoinjector drug delivery device 10' includes a housing 12' defining a shell and having an inner volume 12*a'* and a first end 12*b'*, a needle insertion mechanism 20', an activation mechanism 30', and a drive system 100', each of which may be at least partially disposed within the housing 12'. Further, the drug delivery device 10' may include a controller 14' and an actuator 16' (e.g., a depressible button) that is arranged on an exterior of the housing 12'.

The drive system 100' includes similar features as the previously-described drive system 100 illustrated in FIGS. 2 and 3 such as, for example, a pressure chamber 110', a primary container 120', and a pressurized fluid 102'. The pressure chamber 110' has an outer surface 110*a'*, an inner surface 110*b'* that defines an interior volume 111', a first end 110*c'*, and a second end 110*d'*. The primary container 120' has an outer surface 120*a'*, an inner surface 120*b'* that defines an interior volume 121', a first end 120*c'*, and a second end 120*d'*. As before, the pressurized fluid 102' at least partially surrounds the outer surface 120*a'* of the primary container 120'

In this example, the needle insertion mechanism 20' includes a needle or cannula 22' that is operably coupled to the primary container 120' and/or the pressure chamber 110'. Upon actuation of the actuator 16', the pressure chamber 110' and the primary container 120' are urged towards the first end 12*b'* of the housing 12'. This urging force may be generated using any number of approaches such as, for examples, drive members such as springs coupled to the activation mechanism 30' and/or by manually depressing the actuator 16'. Other examples are possible.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 146B7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); Vectibix® (panitumumab), Xgeva® (denosumab), Prolia® (denosumab), Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153, 507); Tysabri® (natalizumab, anti-α4integrin mAb); Valortim® (MDX-1303, anti-*B. anthracis* protective antigen mAb); ABthrax™; Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-a581 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/1L23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, or BPS 804 (Novartis) and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoVEXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BITE®) antibodies such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A drive system for a drug delivery device, the drive system comprising:
  a pressure chamber having an outer surface and an inner surface defining an interior volume;
  a sealing member at least partially disposed within the interior volume of the pressure chamber;
  a primary container having an outer surface and an inner surface defining an interior volume to store a medicament to be administered to a user, the primary container being at least partially disposed within the interior volume of the pressure chamber; and
  a pressurized fluid predisposed in the interior volume of the pressure chamber, wherein prior to engaging the drive system to administer the medicament to the user, the pressurized fluid is pressurized to exert a compressive preloading pressure on at least a portion of the outer surface of the primary container;
  wherein the sealing member is adapted to fluidly isolate the interior volume of the pressure chamber and the pressurized fluid therein from the interior volume of the primary container.

2. The drive system of claim 1, further comprising an insertion mechanism in fluid communication with the primary container, the insertion mechanism including a needle or a cannula to be inserted into the user to deliver the medicament.

3. The drive system of claim 2, further comprising:
  (a) an activation mechanism in fluid connection with the insertion mechanism and the primary container, the activation mechanism adapted to cause the insertion mechanism to insert the needle or cannula into the user and to cause the medicament to be dispensed, and/or
  (b) a septum disposed at an end of the pressure chamber, wherein upon piercing the septum, a fluid flow path is formed from the interior volume of the primary container to the needle or cannula.

4. The drive system of claim 1, further comprising a stopper member at least partially disposed within the interior volume of the pressure chamber to retain the pressurized fluid within the interior volume of the pressure chamber.

5. The drive system of claim 1, wherein the pressure chamber is constructed from at least one of a transparent or a translucent material.

6. The drive system of claim 1, wherein the pressurized fluid is at least one of water, a silicone oil, or a silicone gel.

7. The drive system of claim 1, wherein the pressurized fluid is pressurized to a pressure level that is a fraction of a failure point of the primary container.

8. A method of reducing damage to a primary container of a drug delivery device, the method comprising:
providing a pressure chamber having an outer surface and an inner surface defining an interior volume;
disposing a primary container in the interior volume of the pressure chamber, the primary container having an outer surface and an inner surface defining an interior volume to store a medicament to be administered to a user;
pressurizing a fluid to a desired fluid compressive preloading pressure value;
prior to engaging the drug delivery device to administer the medicament to the user, disposing the pressurized fluid in the pressure chamber such that the pressurized fluid at least partially surrounds at least a portion of the outer surface of the primary container while exerting the desired compressive preloading fluid pressure value on the primary container;
disposing a sealing member within the interior volume of the pressure chamber such that the sealing member fluidly isolates the interior volume of the pressure chamber and the pressurized fluid therein from the interior volume of the primary container.

9. The method of claim 8, further comprising plugging an end of the pressure chamber with a stopper member upon the fluid being pressurized to the desired compressive preloading pressure value.

10. The method of claim 8, wherein the fluid is pressurized to the desired compressive preloading pressure value via a fluid flow device set to generate a fluid flow at a desired flow rate corresponding to the desired compressive preloading pressure value.

11. The method of claim 10, wherein the desired flow rate is determined via at least one of a pressure gauge or a force transducer.

12. The method of claim 8, wherein the fluid is at least one of water, a silicone oil, or a silicone gel.

13. The method of claim 8, wherein the desired compressive preloading pressure value is a fraction of a failure point of the primary container.

14. A drug delivery device comprising:
a housing defining a shell and an inner volume;
a pressure chamber at least partially disposed within the inner volume of the housing, the pressure chamber having an outer surface and an inner surface defining an interior volume;
a sealing member at least partially disposed within the interior volume of the pressure chamber;
a primary container having an outer surface and an inner surface defining an interior volume to store a medicament to be administered to a user, the primary container being at least partially disposed within the interior volume of the pressure chamber;
a pressurized fluid predisposed in the interior volume of the pressure chamber, wherein the pressurized fluid is pressurized to exert a compressive preloading pressure on at least a portion of the outer surface of the primary container;
an insertion mechanism in fluid communication with the primary container, the insertion mechanism including a needle or a cannula to be inserted into the user to deliver the medicament;
an activation mechanism in fluid connection with the insertion mechanism and the primary container, the activation mechanism adapted to cause the insertion mechanism to insert the needle or cannula into the user and to cause the medicament to be dispensed;
a fluid flow connection coupled to the primary container and the needle or cannula, the fluid flow connection adapted to allow the medicament to flow from the primary container to the needle or cannula;
wherein the pressurized fluid is predisposed in the interior volume of the pressure chamber and is pressurized prior to the activation mechanism being activated to cause the insertion mechanism to insert the needle or cannula into the user and to cause the medicament to be dispensed;
wherein the sealing member is adapted to fluidly isolate the interior volume of the pressure chamber and the pressurized fluid therein from the interior volume of the primary container.

15. The drug delivery device of claim 14, further comprising:
(a) a septum disposed at an end of the pressure chamber, wherein upon piercing the septum, a fluid flow path is formed from the interior volume of the primary container to the needle or cannula and/or
(b) a stopper member at least partially disposed within the interior volume of the pressure chamber to retain the pressurized fluid within the interior volume of the pressure chamber.

16. The drug delivery device of claim 14, wherein the pressure chamber is constructed from at least one of a transparent or a translucent material.

17. The drug delivery device of claim 14, wherein the pressurized fluid is at least one of water, a silicone oil, or a silicone gel.

18. The drug delivery device of claim 14, wherein the pressurized fluid is pressurized to a compressive preloading pressure level that is a fraction of a failure point of the primary container.

* * * * *